United States Patent [19]

Bader et al.

[11] Patent Number: 4,683,034
[45] Date of Patent: Jul. 28, 1987

[54] PROCESS FOR SEPARATING DIMETHYL ISOPHTHALATE AND DIMETHYL ORTHOPHTHALATE FROM THEIR MIXTURE WITH DIMETHYL TEREPHTHALATE

[75] Inventors: Rolf Bader, Dietzenbach; Hartmut Last, Offenbach am Main; Manfred Mayer, Niedernhausen; Siegbert Rittner, Mörfelden-Walldorf; Edgar Wetzel, Heusenstamm, all of Fed. Rep. of Germany

[73] Assignee: Hoechst Aktiengesellschaft, Fed. Rep. of Germany

[21] Appl. No.: 766,767

[22] Filed: Aug. 16, 1985

[30] Foreign Application Priority Data

Aug. 20, 1984 [DE] Fed. Rep. of Germany ....... 3430555

[51] Int. Cl.$^4$ .......................... B01D 9/00; C07C 67/52
[52] U.S. Cl. ......................................... 203/43; 203/47; 203/48; 203/81; 23/297; 62/532; 159/47.1; 560/78
[58] Field of Search ...................... 203/48, 47, 43, 98, 203/94, 39, 74, 81; 560/78; 62/542, 544, 532; 23/297, 299, 295 R, 296; 159/47.1, DIG. 5

[56] References Cited

U.S. PATENT DOCUMENTS

| | | | |
|---|---|---|---|
| 2,890,239 | 6/1959 | Quigg | 560/78 |
| 3,073,754 | 1/1963 | Aroyan et al. | 560/78 |
| 3,076,019 | 1/1963 | Baldwin | 560/78 |
| 3,399,227 | 8/1968 | Tapulionis | 560/78 |
| 3,600,430 | 8/1971 | Martin | 260/475 R |
| 3,836,573 | 9/1974 | Schreiber et al. | 560/78 |
| 3,962,315 | 6/1976 | Achsel | 260/475 B |
| 4,040,793 | 8/1977 | Achsel | 23/273 R |
| 4,126,755 | 11/1978 | Bunger et al. | 560/78 |

FOREIGN PATENT DOCUMENTS 2323219 11/1974 Fed. Rep. of Germany .

OTHER PUBLICATIONS

Winnacker-Kuechler *Chemische Technologie*, 4th Ed., vol. 6, Carl Hanser Verlag, Munich, 1982, p. 148.

*Primary Examiner*—Wilbur Bascomb
*Attorney, Agent, or Firm*—Connolly and Hutz

[57] ABSTRACT

The invention relates to a process for separating dimethyl isophthalate (DMI) and dimethyl orthophthalate (DMO) and other by-products from their mixture with dimethyl terephthalate (DMT), formed in the oxidation of p-xylene followed by esterification with methanol, by crystallization from the melt.

Initially, the esterification product is here distilled once or several times. The DMT-rich fraction obtained is then subjected wholly or partially to one or several crystallizations from the melt, and the DMI-DMO fraction thus obtained is at least partially removed from the system. As an alternative, the DMT-rich fraction is first recrystallized from methanol, the methanol is then evaporated from the mother liquor and the remaining residue is subjected to one or several crystallizations from the melt. The DMI-DMO fraction thus obtained is again at least partially removed from the system.

16 Claims, 4 Drawing Figures

PROCESS FOR SEPARATING DIMETHYL ISOPHTHALATE AND DIMETHYL ORTHOPHTHALATE FROM THEIR MIXTURE WITH DIMETHYL TEREPHTHALATE

The invention relates to a process for separating dimethyl isophthalate (DMI) and dimethyl orthophthalate (DMO) and other by-products from their mixture with dimethyl terephthalate (DMT), formed in the oxidation of p-xylene followed by esterification with methanol.

In this DMT process, which is the most important on a large industrial scale, a liquid-phase oxidation, catalyzed by cobalt salt, of the p-xylene is first carried out with oxygen-containing gases. The p-xylene employed in this process has a purity of more than 99%. The impurities (less than 1%) in the p-xylene comprise, inter alia, the isomers m-xylene and o-xylene in varying quantities. The DMT produced therefore contains corresponding quantities of the isomers DMI and DMO.

The oxidation of p-xylene stops at the stage of p-toluic acid. The (single) carboxyl group of the latter is esterified with methanol, methyl p-toluate (PTE) being formed. Its methyl group is then oxidized to the carboxyl group and the latter is then esterified, DMT thus being being formed.

The two oxidation stages and likewise the two esterification stages can be combined (Witten, Hercules, California Research): a mixture of p-xylene and methyl p-toluate (PTE) is oxidized, and the resulting mixture of p-toluic acid and monomethyl terephthalate is then esterified to methyl p-toluate (PTE) and dimethyl terephthalate (DMT). The two esters are separated by distillation. The PTE is recycled into the oxidation, whereas the DMT is further purified.

However, the two oxidations and two esterifications can also be combined in one stage (BASF, Du Pont and Montecantini). The methanol used as the solvent for the oxidation subsequently esterifies the oxidized methyl groups in one and the same reactor. The latter is operated by the counter-current principle, p-xylene and recycled partial oxidation products being fed in from above, and methanol and air being fed in from below. At 100°–200° C. and 5–20 bar, the oxidation is carried out by means of cobalt salts with a residence time of 22 hours.

The crude DMT obtained from both methods must be distilled and recrystallized in order to obtain pure DMT.

In both methods, however, the DMT isomers dimethyl isophthalate (DMI) and dimethyl orthophthalate (DMO) are also formed in accordance with the fraction of o-xylene and m-xylene, as mentioned, in the feed p-xylene.

In both cases, the problem of removing DMI and DMO from the system arises, and this will be illustrated, taking the abovementioned Witten process as an example.

A mixture of p-xylene and PTE is oxidized in the liquid phase under pressure and at 140°–170° C. with air in the presence of a cobalt-containing catalyst. The oxidation product comprises p-toluic acid and monomethyl terephthalate as well as a little terephthalic acid. The oxidation product is then esterified with methanol, for example at 240° C. and 30–40 bar, and then separated in a so-called crude ester distillation into a PTE-rich fraction, a DMT-rich fraction and a distillation residue which contains the high-boiling by-products of the process (for example diphenyl compounds). The PTE-rich fraction is recycled into the oxidation. The DMT-rich fraction is fed to the downstream purifications which as a rule comprise a rectification and two recrystallizations from methanol. Since the boiling points of the isomers DMI and DMO, contained in this fraction, differ only a little from that of DMT, a separation from DMT succeeds only at the stage of the recrystallization from methanol. In the latter, DMI and DMO pass into the mother liquor which also contains, in solution: residual DMT, residual PTE (which was incompletely separated off in the crude ester distillation) and further partial oxidation products, such as 4-carbomethoxybenzaldehyde and its dimethyl acetal.

p-Toluate (PTE), 4-carbomethoxybenzaldehyde and its dimethyl acetal are DMT intermediates. For this reason, the residue remaining after evaporation of the methanol from the mother liquor (also described below in brief as "mother liquor residue" or "evaporated mother liquor") is recycled into the oxidation. However, this necessarily involves the simultaneous recycle of substances which are not DMT intermediates, but have already been oxidized and esterified twice, namely DMT itself and its two isomers. These substances are therefore to be regarded as a ballast in the process. Since DMT is continuously removed as the desired product from the system in the recrystallization, its fraction does not rise above a certain level, in spite of the recycle. By contrast, DMI and DMO remain as undesired substances in the mother liquor during the recrystallization and are more and more enriched, unless they are removed from the system in some way. In the course of years, they then claim steadily increasing proportions in the production streams. The consequence is not only an overloading of the reactors and rectifications, but also an increasing inefficiency of the recrystallization, which manifests itself in such a way that a predominant fraction of the impurities remaining in the recrystallized DMT is composed of DMI and DMO. The "crude DMT" fed to the recrystallization can then have DMI-DMO contents of 20% by weight, the corresponding content in the mother liquor being up to 50% by weight.

In order to prevent an undue rise of the DMI-DMO level in the plant, that quantity of DMI and DMO must be removed from the system, starting at a certain point, which is continuously re-formed in the plant as a function of the isomer content of the p-xylene fed. In practice, this can be accomplished, for example, by discarding a part of the evaporated mother liquor of the recrystallization. In this case, however, DMT losses must be accepted, which are the higher, the lower the intended DMI-DMO level in the plant. In the case of a DMI-DMO content of 50% by weight in the mother liquor, 1 kg of DMT (and intermediates) is also discarded per kg of DMI-DMO, which may just appear to be still acceptable. If a Lower DMI-DMO level in the plant is to be maintained, the enrichment of DMI and DMO in the mother liquor of the recrystallisation is of course correspondingly lower. The removal of DMI and DMO from the system by discarding evaporated mother liquor thus involves increasingly greater losses with decreasing DMI-DMO level and finally becomes intolerable: whereas, in the abovementioned case of a DMI-DMO content of 20% by weight in the DMT to be recrystallized, the resulting yield reduction is about 0.1%, a yield loss of about 0.7% would have to be accepted at the lower DMI-DMO content of 5% by weight in the DMT to be recrystallized. In order to prevent excessive losses with the removal of DMI-DMO from the system, it is therefore necessary to maintain a high DMI-DMO level, but this entails a high ballast fraction in the circulation.

The present invention relates to a removal of DMI and DMO from the system, which entails low losses even in the case of a low DMI-DMO level. Depending on the isomer content of the p-xylene fed, the yield losses amount to only 0.05%, virtually independently of the DMI-DMO level in the plant.

In this way, the DMI and DMO ballast in the plant can be substantially reduced, enabling the production capacity to be fully utilized.

In the process according to the invention a DMI-DMO concentrate is obtained by subjecting and evaporated mother liquor (under methanol recrystallization) or a part thereof, or the DMT-rich fraction from the abovementioned crude ester distillation or a part of this fraction, to one or several crystallizations from the melt. The DMI-DMO concentrate preferably has an almost eutectic composition and therefore a low DMT content, and it can therefore be removed from the system without substantial DMT losses arising.

BRIEF DESCRIPTION OF THE DRAWING

In the accompanying drawing.

Figure 1:
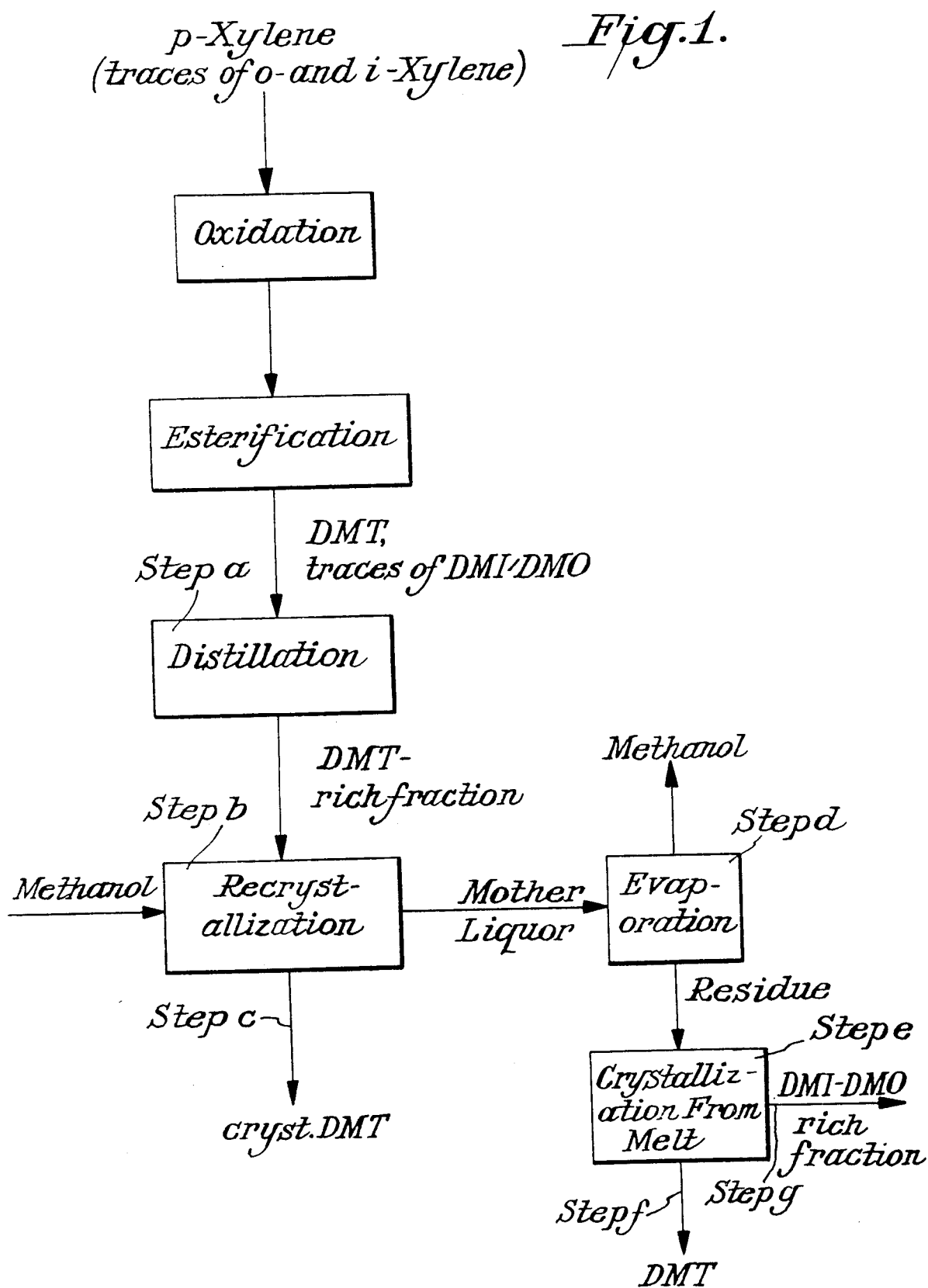
FIG. 1 is a schematic block diagram setting forth a flow sheet illustrating a first preferred embodiment of the DMT-byproduct separation process of this invention.

DETAILED DESCRIPTION OF THE DRAWING AND THE PREFERRED EMBODIMENTS ILLUSTRATED THEREIN

As illustrated in FIG. 1, one embodiment of the present invention is a process for separating dimethyl isophthalate (DMI) and dimethyl orthophthalate (DMO) and other by-products from their mixture with dimethyl terephthalate (DMT), formed in the oxidation of p-xylene followed by esterification with methanol, (a) the esterification product being distilled once or several times, (b) the DMT-rich fraction obtained in step (a) being recrystallized from methanol, (c) the crystalline DMT obtained in step (b) being taken off, and (d) the methanol being evaporated from the mother liquor of step (b), which process comprises (e) melting the residue obtained in step (d) and composed mainly of DMT, DMI and DMO, and causing DMT to crystallize out by cooling, without the DMT content in the by-products reaching the eutectic composition, (f) taking off the DMT obtained in step (e) and (g) at least partially removing the DMI-DMO fraction, obtained in step (e), from the system.

Thus, according to this method, the entire residue of the mother liquor is subjected to one or several crystallizations from the melt.

In step (a), preferably two distillations are carried out. In the first distillation (crude ester distillation), methyl p-toluate (PTE) and high-boilers are separated off from DMT; the PTE is recycled into the oxidation stage. In the second distillation, the DMT-rich fraction thus obtained is rectified.

In step (b), two recrystallizations from methanol are in general carried out.

In step (e), the eutectic point is preferably approached as closely as possible (but without reaching it), in order to obtain the highest possible enrichment of the by-products, in particular DMI and DMO. Since the by-products then have almost the eutectic composition, they contain only very little DMT.

The procedure in detail is as follows: the residue of the mother liquor is melted and then, preferably within 0.5 to 2 hours, first cooled to a temperature which is 0.5° to 15° C. below the solidification point of the starting mixture.

The optimum temperature, to which the cooling is taken here, depends on the nature and quantity of the diverse impurities, and also on the crystallization apparatus used. At the selected temperature, the crystals are allowed to grow for a few minutes up to a few hours, depending on the crystallization apparatus used, and the system is then cooled down further, preferably approaching the eutectic temperature, but without reaching it. In particular, cooling is taken to a temperature which is only 0.5° to 3° C. above the eutectic temperature. That temperature is here termed the eutectic temperature at which the particular eutectic mixture, dependent on the nature of the impurity in the DMT, separates out. The fraction which has remained liquid is separated from the crystals, the liquid impurities adhering in and on the crystals are separated off by raising the temperature as uniformly as possible, and the DMT thus purified is obtained by further melting.

In the purification in a static plate crystallizer or tube crystallizer (drip apparatus), as described in Winnacker-Küchler, Chemische Technologie [Chemical Technology], 4th Edition, Volume 6, 1982, page 148, the cooling is preferably first taken down only to 1.5° to 3° C. below the solidification point of the starting mixture and this temperature is maintained for 1-3 hours in order to obtain good crystal formation.

This system is then cooled down further, preferably within 2 to 20 hours, in particular 4 to 10 hours, and preferably down to the vicinity of the eutectic temperature. The impurities which then have still remained liquid in the crystallizer are separated off, and the remaining crystal mass is purified further by raising the temperature. This rise in temperature should take place slowly, preferably at a rate of rise of about 0.5° to 2° C. per hour. The liquid fractions obtained at the beginning of this melting process are separated off and subjected to a further crystallization from the melt. The crystal mass finally remaining in the apparatus represents the isolated DMT.

If this procedure is carried out in a single stage or (preferably) in several stages using the trickle film crystallizer described in U.S. Pat. No. 3,621,664, the mixtures are preferably cooled here first for a few minutes to a temperature of about 1° to 10° C. below the solidification point of the starting mixture. Further cooling then takes place, preferably within 0.5 to 3 hours, in particular within 0.5 to 1.5 hours, and preferably again down to the vicinity of the eutectic temperature. The crystals are then separated off from the remaining liquid fraction. Further purification is then effected by an exudation step with the crystals at rising temperature. The dimethyl terephthalate thus isolated is then melted by further heating and drained from the apparatus or, if necessary, subjected to a further crystallization from the melt.

The optimum temperatures for initiating the crystallization, provision for good crystal growth in order to separate off the impurities effectively, and the most favorable crystallization times can readily be determined for each starting mixture by a preliminary test, according to the explanations given above.

Since the object of step (e) is the highest possible concentration of DMI and DMO and the lowest possible concentration of DMT in the by-product fraction (DMI-DMO fraction) of the crystallization from the melt, the DMT crystallizing out generally still contains residual by-products. In general, it is therefore then recrystallized from methanol and, in particular, preferably together with the DMT-rich fraction from step (a).

Any part of the DMI-DMO fraction which may not have been removed from the system in step (g) is recycled into the oxidation stage because of its content of partially oxidized DMT intermediates (4-carbomethoxybenzaldehyde and the dimethyl acetal thereof, and p-toluate). Preferably, only about 5–15% by weight of the DMI-DMO fraction are removed from the system and the remainder is recycled. It is also possible, however, to distill this remainder and then to recycle only the partially oxidized DMT intermediates.

Figure 2:
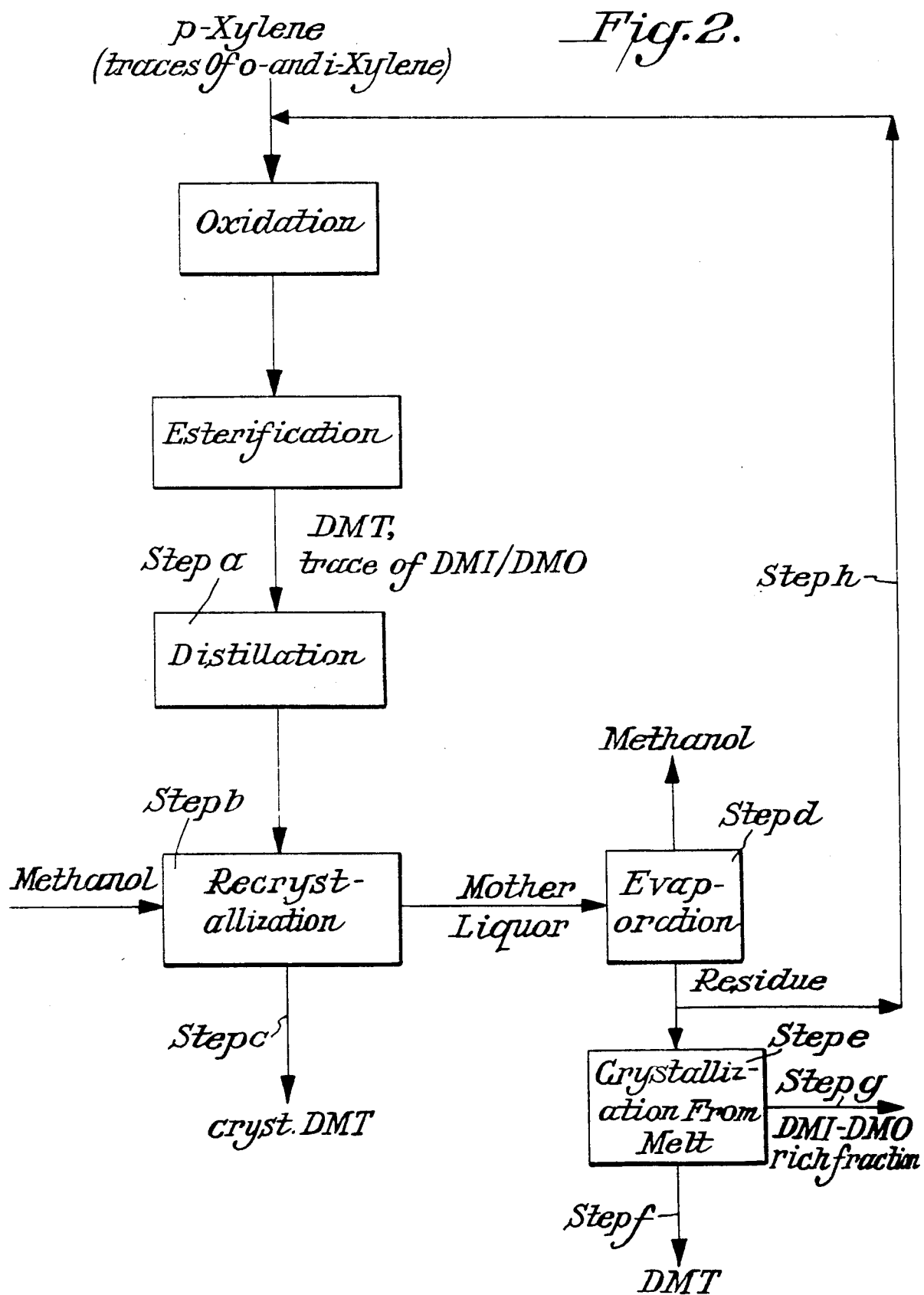
FIG. 2 is a schematic block diagram setting forth a flow sheet illustrating a second preferred embodiment of the DMT-byproduct separation process of this invention.

Instead of the total residue of the mother liquor (of the recrystallization from methanol), a part thereof can also be subjected to one or several crystallizations from the melt. As illustrated in FIG. 2, a second embodiment of the invention is therefore a process for separating dimethyl isophthalate (DMI) and dimethyl orthophthalate (DMO) and other by-products from their mixture with dimethyl terephthalate (DMT), formed in the oxidation of p-xylene followed by esterification with methanol, (a) the esterification product being distilled once or several times, (b) the DMT-rich fraction obtained in step (a) being recrystallized from methanol, (c) the crystalline DMT obtained in step (b) being taken off, and (d) the methanol being evaporated from the mother liquor of step (b), which process comprises (e) melting a part of the residue obtained in step (d) and composed mainly of DMT, DMI and DMO, and causing DMT to crystallize out by cooling, without the DMT content in the byproducts reaching the eutectic composition, (f) taking off the DMT obtained in step (e), (g) removing the DMI-DMO fraction, obtained in step (e) from the system, and (h) recycling the part, not used in step (e), of the residue obtained in step (d) into the oxidation stage.

In this method, a part of the residue of the mother liquor is thus recycled into the oxidation in accordance with the state of the art, and the other part is used for removing DMI and DMO from the system by means of crystallization from the melt. This leads to reduced capacities of the required apparatus for crystallization from the melt, as compared with the first-described method.

The details already given for the first method again apply to steps (a), (b) and (e), with the exception that only a part of the residue from the mother liquor is now used in step (e). The part not used here is recycled into the oxidation stage in accordance with step (h).

The quantity of the residue used in step (e) depends on the re-formation rate of DMI and DMO, which is in turn determined by the isomer content of the feed p-xylene. With a p-xylene quality of over 99%, as usually traded on the world market, preferably 5–15% by weight of the residue from the mother liquor are used in step (e), if it is desired to hold a level of about 3–5% of DMI and DMO in the DMT-rich fraction from step (b). If a smaller fraction of the residue from the mother liquor is used in step (e), correspondingly higher DMI-DMO levels will be established.

Figure 3:
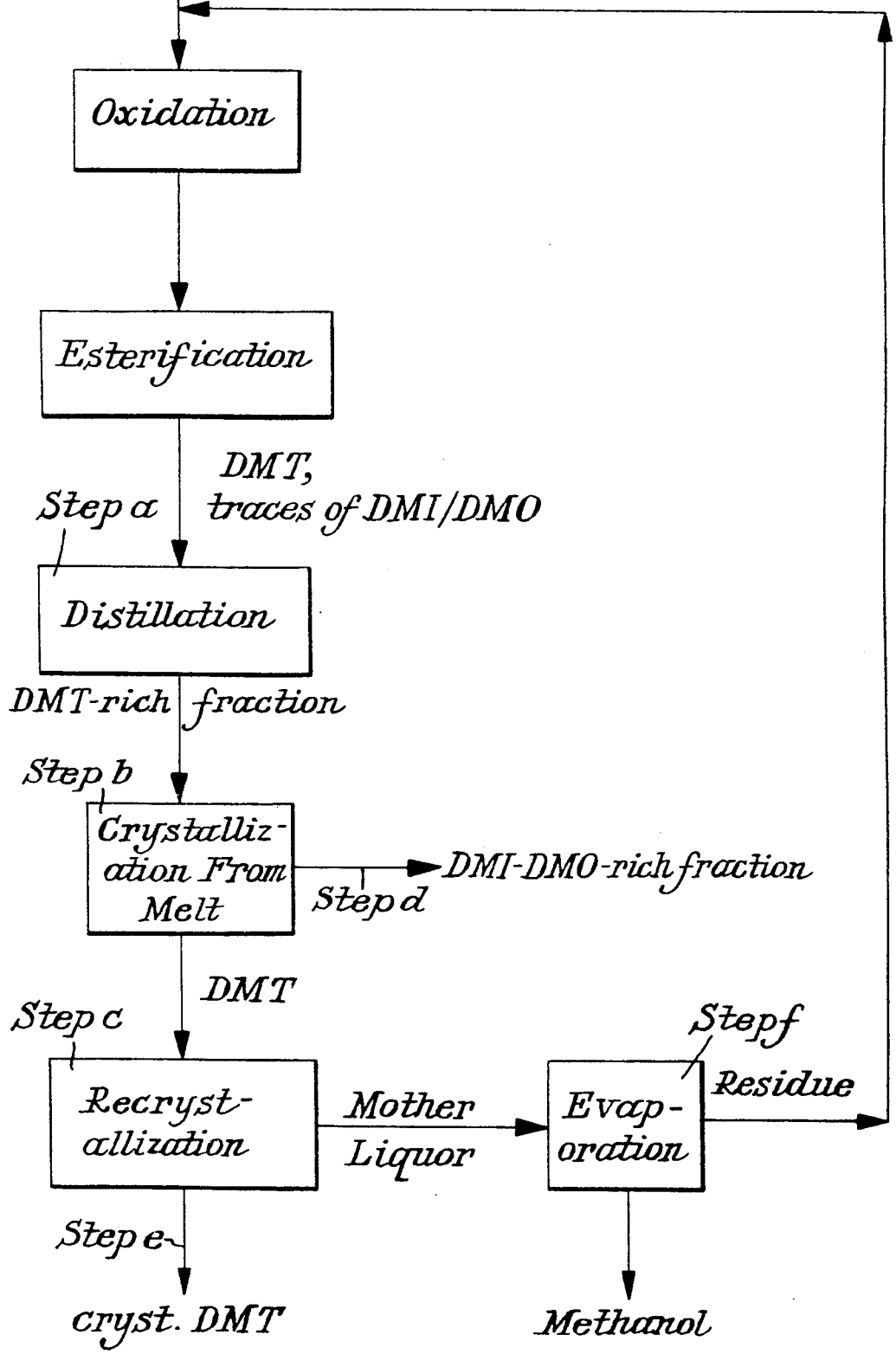
FIG. 3 is a schematic block diagram setting forth a flow sheet illustrating a third embodiment of the DMT-byproduct separation process of this invention.

The mother liquor from the recrystallization from methanol is that mixture in the plant which has the highest concentration of DMI and DMO. The residue from the mother liquor is therefore preferably utilized for removing DMI and DMO from the system. This is the basis of the two methods just described. However, the DMT-rich fraction, which is recrystallized from methanol according to the state of the art and also according to the two above methods (step b) in each case), also has a relatively high DMI-DMO concentration and can therefore be utilized for removing these substances from the system. Either the entire DMT-rich fraction or a part thereof can be subjected to one or several crystallizations from the melt. As illustrated in FIG. 3, a third embodiment of the invention is therefore a process for separating dimethyl isophthalate (DMI) and dimethyl orthophthalate (DMO) and other by-products from their mixture with dimethyl terephthalate (DMT), formed in the oxidation of p-xylene followed by esterification with methanol, (a) the esterification product being distilled once or several times, which process comprises (b) melting the DMT-rich fraction obtained in step (a) and causing DMT to crystallize out by cooling, without the DMT content in the by-products reaching the eutectic composition, (c) recrystallizing the DMT obtained in step (b) from methanol, (d) at least partially removing the DMI-DMO fraction, obtained in step (b), from the system, (e) taking off the crystalline DMT obtained in step (c), and (f) evaporating the methanol from the mother liquor of step (c) and recycling the residue into the oxidation stage.

The DMT obtained in step (b) is already relatively pure, so that the recrystallization from methanol in step (c) is greatly facilitated. In most cases, only one recrystallization suffices here, whereas two recrystallizations were necessary according to the state of the art.

Any part of the DMI-DMO fraction which may not have been removed in step (d) is recycled into the oxidation stage. Preferably, only about 5–15% by weight are removed from the system and the remainder is recycled.

The same explanations as given on this topic under the first two methods (where the crystallization from the melt represents step (e) in each case) apply to the crystallization from the melt, which is here carried out as step (b).

Figure 4:
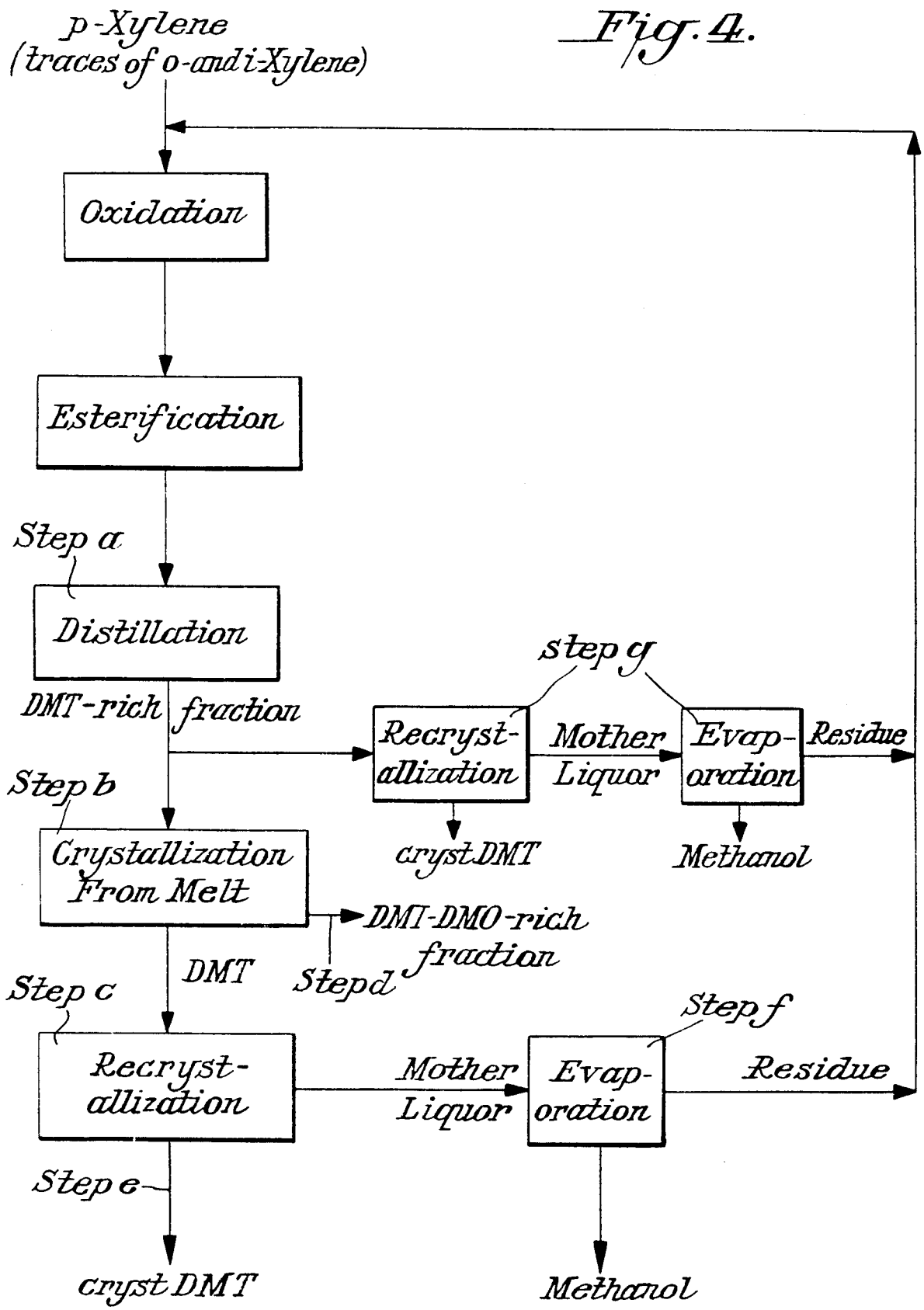
FIG. 4 is a schematic block diagram setting forth a flow sheet illustrating a fourth emodiment of the DMt-byproduct separation process of this invention.

Instead of the entire DMT-rich fraction from the distillation of the esterification product, it is also possible to subject a part thereof to the crystallization from the melt. As illustrated in FIG. 4, a fourth embodiment of the invention is therefore a process for separating dimethyl isophthalate (DMI) and dimethyl orthophthalate (DMO) and other by-products from their mixture with dimethyl terephthalate (DMT), formed in the oxidation of p-xylene followed by esterification with methanol, (a) the esterification product being distilled once or several times, which process comprises (b) melting a part of the DMT-rich fraction obtained in step (a) and causing DMT to crystallize out by cooling, without the DMT content in the by-products reaching the eutectic composition, (c) recrystallizing the DMT obtained in step (b) from methanol, (d) removing the DMI-DMO fraction, obtained in step (b) from the system, (e) taking off the crystalline DMT obtained in step (c), (f) evaporating the methanol from the mother liquor of step (c) and recycling the residue into the oxidation stage, and (g) recrystallizing the part, not used in step (b), of the DMT-rich fraction obtained in step (a) from methanol, taking off the crystalline DMT thus obtained, evaporating the methanol from the mother liquor and recycling the residue into the oxidation stage.

The explanations given before again apply to step (a), and also for the crystallization from the melt, carried out as step (b). In step (c), a single recrystallization again suffices in general. Preferably, 5–15% by weight of the DMT-rich fraction obtained in step (a) are used in step (b). The remainder is used in step (g). Two recrystallizations are preferably carried out in step (g).

The invention is illustrated by the Examples which follow, without being restricted thereby. The percentages figures are always per cent by weight.

EXAMPLE 1

In a tube crystallizer, the jacket of which is connected to a thermostat and to a time program controller for the temperature, 532 g of a methanol-free residue from the recrystallization of DMT with methanol, having a solidification point of 87° C. and the following composition, are used:

Dimethyl terephthalate (DMT): 29.0%
Dimethyl isophthalate (DMI): 56.3%
Dimethyl orthophthalate (DMO): 4.7%
4-Carbomethoxybenzaldehyde dimethyl acetal: 3.0%
4-Carbomethoxybenzaldehyde: 1.1%
Methyl p-toluate (PTE): 5.8%
Methyl benzoate: 0.1%

The mixture is cooled to 85.5° C., the crystallization starting promptly. After about one hour at 84°–85.5° C., the system is cooled to 30° C. in the course of 12 hours and the crystallizer is then opened. The fraction which has remained liquid is allowed to run out and the temperature of the crystal mass remaining in the crystallizer is slowly raised to 68° C., the melt which drips off during this step being combined with the melt which has already run off at 30° C. This gives 140 g of crystallizate having a solidification point of 133.4° C. and 390 g of crystallization residue having a solidification point of 64.5° C. This residue had the following composition:

Dimethyl terephthalate (DMT): 14.5%
Dimethyl isophthalate (DMI): 64.0%
Dimethyl orthophthalate (DMO): 8.1%
4-Carbomethoxybenzaldehyde dimethyl acetal: 4.9%
4-Carbomethoxybenzaldehyde: 2.01%
Methyl p-toluate (PTE): 6.4%
Methyl benzoate: 0.1%

EXAMPLE 2

In a crystallizer as described in U.S. Pat. No. 3,621,664, 29.8 kg of a methanol-free residue from the recrystallization of DMT with methanol, having a solidification point of 89.2° C. and the following composition, were used for crystallization from the melt:

Dimethyl terephthalate (DMT): 30.7%
Dimethyl isophthalate (DMI): 54.1%
Dimethyl orthophthalate (DMO): 5.6%
4-Carbomethoxybenzaldehyde dimethyl acetal: 3.2%
4-Carbomethoxybenzaldehyde: 1.1%
Methyl p-toluate (PTE): 5.2%
Methyl benzoate: 0.1%

This mixture was crystallized at down to 20° C. (temperature of the cooling medium) for 100 minutes. This gave a crystallizate (7.9 kg) having a solidification point of 124° C. and a crystallization residue (21.9 kg) having a solidification point of 63° C. This residue had the following composition:

Dimethyl terephthalate (DMI): 15.15%
Dimethyl isophthalate (DMI): 60.8%
Dimethyl orthophthalate (DMO): 9.6%
4-Carbomethoxybenzaldehyde dimethyl acetal: 5.5%
4-Carbomethoxybenzaldehyde: 2.03%
Methyl p-toluate (PTE): 6.82%
Methyl benzoate: 0.1%

EXAMPLE 3

In a crystallizer as described in U.S. Pat. No. 3,621,664, 20 kg of crystallization residue having a solidification point of 63° C. from the crystallization of Example 2 were used for crystallization from the melt.

This mixture was crystallized in the temperature range down to 0° C. (temperature of the cooling medium) for 120 minutes. This gave 5.8 kg of crystallisate having a solidification point of 106° C. and 14.2 kg of crystallization residue having a solidification point of 49° C. The DMT content is this residue (with dimethyl isophthalate, dimethyl orthophthalate, 4-carbomethoxybenzaldehyde dimethyl acetal, 4-carbomethoxybenzaldehyde and methyl p-toluate as accompanying substances) was then only about 10%.

We claim:

1. A process for separating dimethyl isophthalate (DMI) and dimethyl orthophthalate (DMO) and other by-products from their mixture with dimethyl terephthalate (DMT), formed in the oxidation of p-xylene followed by esterification with methanol, which comprises:

(a) distilling the esterification product to obtain a solid DMT-rich fraction;

(b) recrystallizing the DMT-rich fraction obtained in step (a) from methanol to obtain crystalline DMT and mother liquor;

(c) recovering the crystalline DMT obtained in step (b);

(d) evaporating the methanol from the mother liquor of step (b) to obtain a solid residue composed mainly of DMI, DMI and DMO;

(e) melting the residue obtained in step (d) and then cooling the resulting melt, without the DMT content in the melt reaching the eutectic content to crystallize DMT, to obtain DMT and a DMI-DMO-rich fraction;

(f) recovering the DMT obtained in step (e); and (g) at least partially removing the DMI-DMO-rich fraction, obtained in step (e).

2. The process as claimed in claim 1, wherein, in step (e), the melt is first cooled within 0.5 to 2 hours to a temperature which is 0.5° to 15° C. below the solidification point of the melt, the crystals are then allowed to grow and cooling is then taken further, but without reaching the eutectic temperature of the melt.

3. The process as claimed in claim 1, wherein in step (e), cooling is taken down to a temperature which is only 0.5° to 3° C. above the eutectic temperature of the melt.

4. The process as claimed in claim 1, wherein, in step (g), 5–15% by weight of the DMI-DMO-rich fraction is removed and the remainder is recycled into the oxidation stage as a recycle stream, whereby buildup of DMI or DMO concentration in this recycle stream is avoided.

5. A process for separating dimethyl isophthalate (DMI) and dimethyl orthophthalate (DMO) and other by-products from their mixture with dimethyl terephthalate (DMT), formed in the oxidation of p-xylene followed by esterification with methanol, which comprises (a) distilling the esterification product to obtain a solid DMT-rich fraction;

(b) recrystallizing the DMT-rich fraction obtained in step (a) from methanol to obtain crystalline DMT and mother liquor;

(c) recovering the crystalline DMT obtained in step (b);

(d) evaporating the methanol from the mother liquor of step (b) to obtain a solid residue composed mainly of DMI, DMI and DMO;

(e) melting a part of the residue obtained in step (d) and then cooling the resulting melt to crystallize DMT, without the DMT content in the melt reaching the eutectic content, to obtain DMT and a DMI-DMO-rich fraction;

(f) recovering the DMT obtained in step (e);

(g) removing the DMI-DMO-rich fraction, obtained in step (e); and (h) recycling the part, not used in step (e), of the residue obtained in step (d) into the oxidation stage.

6. The process as claimed in claim 5, wherein, in step (e), the melt is first cooled within 0.5 to 2 hours to a temperature which is 0.5° to 15° C. below the solidification point of the melt, the crystals are then allowed to grow and cooling is then taken further, but without reaching the eutectic temperature of the melt.

7. The process as claimed in claim 5, wherein, in step (e), cooling is taken down to a temperature which is only 0.5° to 3° C. above the eutectic temperature of the melt.

8. The process as claimed in claim 5, wherein 5–15% by weight of the residue obtained in step (d) is used to step (e) and the remainder is recycled into the oxidation stage as a recycle stream, whereby buildup of DMI or DMO concentration in this recycle stream is avoided.

9. A process for separating dimethyl isophthalate (DMI) and dimethyl orthophthalate (DMO) and other by-products from their mixture with dimethyl terephthalate (DMT), formed in the oxidation of p-xylene followed by esterification with methanol, which comprises (a) distilling the esterification product to obtain a solid DMT-rich fraction;

(b) melting the DMT-rich fraction obtained in step (a) and then cooling the resulting melt to crystallize DMT, without the DMT content in melt reaching the eutectic content, to obtain DMT and a DMI-DMO-rich fraction;

(c) recrystallizing the DMT obtained in step (b) from methanol to obtain crystalline DMT and mother liquor;

(d) at least partially removing the DMI-DMO-rich fraction, obtained in step (b);

(e) recovering the crystalline DMT obtained in step (c); and (f) evaporating the methanol from the mother liquor of step (c) to obtain a residue composed mainly of DMI, DMI and DMO, and then recycling the residue into the oxidation stage.

10. The process as claimed in claim 9, wherein, in step (b), the melt is first cooled within 0.5 to 2 hours to a temperature which is 0.5° to 15° C. below the solidification point of the melt, the crystals are then allowed to grow and cooling is then taken further, but without reaching the eutectic temperature of the melt.

11. The process as claimed in claim 9, wherein, in step (b), cooling is taken down to a temperature which is only 0.5° to 3° C. above the eutectic temperature of the melt.

12. The process as claimed in claim 9, wherein, in step (d), 5–15% by weight of the DMI-DMO-rich fraction is removed and the remainder is recycled into the oxidation stage as a recycle stream, whereby buildup of DMI or DMO concentration in this recycle stream is avoided.

13. A process for separating dimethyl isophthalate (DMI) and dimethyl orthophthalate (DMO) and other by-products from their mixture with dimethyl terephthalate (DMT), formed in the oxidation of p-xylene followed by esterification with methanol, which comprises (a) distilling the esterification product to obtain a solid DMT-rich fraction;

(b) melting a part of the DMT-rich fraction obtained in Step (a) and then cooling the resulting melt to crystallize DMT, without the DMT content in the melt reaching the eutectic content, to obtain DMT and a DMI-DMO-rich fraction;

(c) recrystallizing the DMT obtained in step (b) from methanol, to obtain crystalline DMT and mother liquor;

(d) removing the DMI-DMO-rich fraction, obtained in step (b);

(e) recovering the crystalline DMT obtained in step (c);

(f) evaporating the methanol from the mother liquor of step (c) to obtain a residue composed mainly of DMI, DMI and DMO and then recycling the residue into the oxidation stage, and (g) recrystallizing the part, not used in step (b), of the DMT-rich fraction obtained in step (a) from methanol to obtain crystalline DMT and mother liquor, recovering the crystalline DMT thus obtained, evaporating the methanol from the mother liquor to obtain a residue composed mainly of DMI, DMI and DMO and recycling the residue into the oxidation stage.

14. The process as claimed in claim 13, wherein, in step (b), the melt is first cooled within 0.5 to 2 hours to a temperature which is 0.5° to 15° C. below the solidification point of the melt, the crystals are then allowed to grow and cooling is then taken further, but without reaching the eutectic temperature of the melt.

15. The process as claimed in claim 1, wherein, in step (b), cooling is taken down to a temperature which is only 0.5° to 3° C. above the eutectic temperature of the melt.

16. The process as claimed in claim 13, wherein 5-15% by weight of the DMT-rich fraction obtained in step (a) is used in step (b) and the remainder is recycled into the oxidation stage as a recycle stream, whereby buildup of DMI or DMO concentration in this recycle stream is avoided.

* * * * *